US011495329B2

(12) United States Patent
Lee

(10) Patent No.: US 11,495,329 B2
(45) Date of Patent: Nov. 8, 2022

(54) APPARATUS AND METHOD FOR DETERMINING VALIDITY OF BIO-INFORMATION ESTIMATION MODEL

(71) Applicant: SAMSUNG ELECTRONICS CO., LTD., Suwon-si (KR)

(72) Inventor: June Young Lee, Seongnam-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 437 days.

(21) Appl. No.: 16/801,283

(22) Filed: Feb. 26, 2020

(65) Prior Publication Data

US 2020/0372975 A1    Nov. 26, 2020

(30) Foreign Application Priority Data

May 20, 2019   (KR) .......................... 10-2019-0058890

(51) Int. Cl.
  *G16B 50/00*   (2019.01)
  *G06N 20/00*   (2019.01)
  *G16B 40/00*   (2019.01)
  *G06N 5/04*    (2006.01)

(52) U.S. Cl.
  CPC .............. *G16B 50/00* (2019.02); *G06N 5/04* (2013.01); *G06N 20/00* (2019.01); *G16B 40/00* (2019.02)

(58) Field of Classification Search
  CPC ........ G16B 50/00; G16B 40/00; G06N 20/00; G06N 5/04; G16H 50/20
  See application file for complete search history.

(56) References Cited

U.S. PATENT DOCUMENTS

| 6,163,154 A | 12/2000 | Anderson et al. |
| 7,809,416 B2 | 10/2010 | Ota et al. |
| 9,087,680 B2 | 7/2015 | Shimada et al. |
| 2003/0191377 A1 | 10/2003 | Robinson et al. |
| 2004/0147034 A1 | 7/2004 | Gore et al. |
| 2004/0185582 A1 | 9/2004 | Kueny |

(Continued)

FOREIGN PATENT DOCUMENTS

| CA | 2 543 487 A1 | 5/2005 |
| JP | 2006277370 A | 10/2006 |
| JP | 201364730 A | 4/2013 |

OTHER PUBLICATIONS

Communication dated Sep. 21, 2020, issued by the European Patent Office in European Application No. 20170525.8.

(Continued)

*Primary Examiner* — Etienne P Leroux
(74) *Attorney, Agent, or Firm* — Sughrue Mion, PLLC

(57) ABSTRACT

An apparatus for determining a validity of a bio-information estimation model includes a data acquirer interface configured to acquire an in vivo spectrum of an object, and acquire bio-information and a concentration of a main component which are estimated based on the in vivo spectrum and a bio-information estimation model; and a processor configured to acquire a residual spectrum of the acquired in vivo spectrum based on the acquired in vivo spectrum, the acquired bio-information, and the acquired concentration of the main component, determine a similarity between the acquired residual spectrum and a reference residual spectrum, and determine the validity of the bio-information estimation model based on the determined similarity.

38 Claims, 11 Drawing Sheets

(56) References Cited

U.S. PATENT DOCUMENTS

| | | |
|---|---|---|
| 2004/0223155 A1 | 11/2004 | Hazen et al. |
| 2006/0167348 A1 | 7/2006 | Arnold et al. |
| 2007/0271055 A1 | 11/2007 | Hagler |
| 2008/0190557 A1 | 8/2008 | Shekel et al. |
| 2011/0035213 A1 | 2/2011 | Malenovsky et al. |
| 2011/0153226 A1 | 6/2011 | Dasaratha et al. |
| 2014/0183353 A1 | 7/2014 | Shimada et al. |
| 2016/0123872 A1 | 5/2016 | Miao et al. |
| 2017/0079565 A1 | 3/2017 | Choi et al. |
| 2017/0177835 A1 | 6/2017 | Cardoso-Menezes et al. |
| 2017/0319185 A1* | 11/2017 | Choi .................... G01N 21/359 |
| 2021/0121108 A1* | 4/2021 | Nashman ........... G01R 33/3808 |

OTHER PUBLICATIONS

Carl A Anderson, et al., "Process Analytical Technology Case Study, Part III: Calibration Monitoring", AAPS PharmSciTech, Feb. 2005, vol. 6, No. 2, Article 39, pp. E284-E297 (Total 15 pages), URL: https://www.researchgate.net/publication/7416075.

* cited by examiner

APPARATUS AND METHOD FOR DETERMINING VALIDITY OF BIO-INFORMATION ESTIMATION MODEL

CROSS-REFERENCE TO RELATED APPLICATION(S)

This application claims priority from Korean Patent Application No. 10-2019-0058890, filed on May 20, 2019, in the Korean Intellectual Property Office, the entire disclosure of which is incorporated herein by reference for all purposes.

BACKGROUND

1. Field

The disclosure relates to technology for determining validity of a bio-information estimation model.

2. Description of Related Art

Diabetes is a chronic disease that may cause various complications and can be difficult or impossible to control or cure, and hence patients with diabetes are advised to check their blood glucose regularly to prevent complications. In particular, when insulin is administered to control a blood glucose level, the blood glucose level should be closely monitored to avoid hypoglycemia and control an insulin dosage. There are several ways to monitor a glucose level, including invasive finger pricking testing and non-invasive glucose monitoring without causing pain. The invasive method may provide high reliability in measurement, but may cause pain and inconvenience as well as an increased risk of infections due to the use of injection to collect blood. Recently, extensive research has been conducted on a method of non-invasive measurement of a blood glucose level using a spectroscope without collecting blood.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

One or more example embodiments provide an apparatus and method for accurately determining validity of a bio-information estimation model that is used to estimate bio-information of an object, thereby increasing accuracy in estimating the bio-information.

According to an aspect of an example embodiment, there is provided an apparatus for determining a validity of a bio-information estimation model, including: a data acquirer interface configured to acquire an in vivo spectrum of an object, and acquire bio-information and a concentration of a main component which are estimated based on the in vivo spectrum and the bio-information estimation model; and a processor configured to acquire a residual spectrum of the acquired in vivo spectrum based on the acquired in vivo spectrum, the acquired bio-information, and the acquired concentration of the main component, determine a similarity between the acquired residual spectrum and a reference residual spectrum, and determine the validity of the bio-information estimation model based on the determined similarity.

The processor may be configured to reconstruct an in vivo spectrum based on the acquired in vivo spectrum, the acquired bio-information, and the acquired concentration of the main component, and acquire the residual spectrum based on the reconstructed in vivo spectrum and the acquired in vivo spectrum.

The processor may be configured to acquire the residual spectrum by subtracting the reconstructed in vivo spectrum from the acquired in vivo spectrum.

The bio-information may include information on a concentration of an analyte, the analyte including at least one of glucose, triglyceride, urea, uric acid, lactate, proteins, cholesterols, antioxidants, and ethanol.

The processor may be configured to select, as the reference residual spectrum, a residual spectrum of an in vivo spectrum that is measured prior to measuring the acquired in vivo spectrum.

The processor may be configured to determine that the bio-information estimation model is invalid based on a comparison between the determined similarity and a predetermined reference value.

The processor may be configured to determine the validity of the bio-information estimation model further based on a size of a vector representing the acquired residual spectrum.

The bio-information estimation model may be based on a net analyte signal (NAS) algorithm.

According to an aspect of an example embodiment, there is provided an apparatus for determining a validity of a bio-information estimation model, including: a data acquirer interface configured to acquire an in vivo spectrum of an object, and acquire bio-information and a concentration of a main component which are estimated based on the in vivo spectrum and the bio-information estimation model; and a processor configured to acquire a residual spectrum of the acquired in vivo spectrum based on the acquired in vivo spectrum, the acquired bio-information, and the acquired concentration of the main component and determine the validity of the bio-information estimation model by based on a change in shape of the residual spectrum over time.

The processor may be configured to reconstruct an in vivo spectrum based on the acquired in vivo spectrum, the acquired bio-information, and the acquired concentration of the main component and acquire the residual spectrum based on the reconstructed in vivo spectrum and the acquired in vivo spectrum.

The processor may be configured to acquire the residual spectrum by subtracting the reconstructed in vivo spectrum from the acquired in vivo spectrum.

The bio-information may include information on a concentration of an analyte, the analyte including at least one of glucose, triglyceride, urea, uric acid, lactate, proteins, cholesterols, antioxidants, and ethanol.

The processor may be configured to determine that the bio-information estimation model is invalid based on the change in shape of the residual spectrum over time exceeding a predetermined reference value.

The processor may be configured to determine the change in shape of the residual spectrum based on a similarity between the acquired residual spectrum and a reference residual spectrum.

The processor may be configured to select, as the reference residual spectrum, a residual spectrum of an in vivo spectrum that is measured prior to measuring the acquired in vivo spectrum.

The processor is configured to determine the validity of the bio-information estimation model further based on a size of a vector representing the acquired residual spectrum.

The bio-information estimation model may be based on a NAS algorithm.

According to an aspect of an example embodiment, there is provided a method of determining a validity of a bio-information estimation model, including: acquiring an in vivo spectrum of an object, and acquiring bio-information and a concentration of a main component which are estimated based on the in vivo spectrum and the bio-information estimation model; acquiring a residual spectrum of the acquired in vivo spectrum based on the acquired in vivo spectrum, the acquired bio-information, and the acquired concentration of the main component; determining a similarity between the acquired in vivo spectrum and a reference residual spectrum; and determining the validity of the bio-information estimation model based on the determined similarity.

The acquiring the residual spectrum may include reconstructing an in vivo spectrum based on the acquired in vivo spectrum, the acquired bio-information, and the acquired concentration of the main component, and acquiring the residual spectrum based on the reconstructed in vivo spectrum and the acquired in vivo spectrum.

The acquiring the residual spectrum may include acquiring the residual spectrum by subtracting the reconstructed in vivo spectrum from the acquired in vivo spectrum.

The bio-information may include information on a concentration of an analyte, the analyte including at least one of glucose, triglyceride, urea, uric acid, lactate, proteins, cholesterols, antioxidants, and ethanol.

The determining the validity may include selecting, as the reference residual spectrum, a residual spectrum of an in vivo spectrum that is measured prior to measuring the acquired in vivo spectrum.

The determining the validity may include determining that the bio-information estimation model is invalid based on the determined similarity being smaller than a predetermined reference value.

The determining the validity may include determining the validity of the bio-information estimation model further based on a size of a vector representing the acquired residual spectrum.

The bio-information estimation model may be based on a NAS algorithm.

According to an aspect of an example embodiment, there is provided a method of determining a validity of a bio-information estimation model, including: acquiring an in vivo spectrum of an object, and acquiring bio-information and a concentration of a main component which are estimated based on the in vivo spectrum and the bio-information estimation model; acquiring a residual spectrum of the acquired in vivo spectrum based on the acquired in vivo spectrum, the acquired bio-information, and the acquired concentration of the main component; and determining the validity of the bio-information estimation model based on a change in shape of the residual spectrum over time.

The acquiring the residual spectrum may include reconstructing an in vivo spectrum based on the acquired in vivo spectrum, the acquired bio-information, and the acquired concentration of the main component and acquiring the residual spectrum based on the reconstructed in vivo spectrum and the acquired in vivo spectrum.

The acquiring the residual spectrum may include acquiring the residual spectrum by subtracting the reconstructed in vivo spectrum from the acquired in vivo spectrum.

The bio-information may include information on a concentration of an analyte, the analyte including at least one of glucose, triglyceride, urea, uric acid, lactate, proteins, cholesterols, antioxidants, and ethanol.

The determining the validity of the bio-information estimation model may include determining that the bio-information estimation model is invalid based on the change in shape of the residual spectrum over time exceeding a predetermined reference value.

The determining the validity may include determining the change in shape of the residual spectrum over time based on a similarity between the acquired residual spectrum and a reference residual spectrum.

The determining the validity may include selecting, as the reference residual spectrum, a residual spectrum of an in vivo spectrum that is measured prior to measuring the acquired in vivo spectrum.

The determining the validity of the bio-information estimation model may include determining the validity of the bio-information estimation model further based on a size of a vector representing the acquired residual spectrum.

The bio-information estimation model may be based on a NAS algorithm.

According to an aspect of an example embodiment, there is provided a method of determining a validity of a bio-information estimation model, including: acquiring an in vivo spectrum of an object; acquiring a residual spectrum of the acquired in vivo spectrum based on the bio-information estimation model; determining a similarity between the acquired residual spectrum and a reference residual spectrum; and determining the validity of the bio-information estimation model based on the determined similarity.

The bio-information estimation model may be based on a NAS algorithm.

The acquiring the residual spectrum may include estimating bio-information of the object and a concentration of a main component based on the acquired in vivo spectrum and the bio-information estimation model, reconstructing an in vivo spectrum based on the acquired in vivo spectrum, the estimated bio-information, and the estimated concentration of the main component, and acquiring the residual spectrum based on the reconstructed in vivo spectrum and the acquired in vivo spectrum.

The acquiring the residual spectrum may include acquiring the residual spectrum by subtracting the reconstructed in vivo spectrum from the acquired in vivo spectrum.

BRIEF DESCRIPTION OF THE DRAWINGS

The above and other aspects and features of the disclosure will become more apparent by describing in detail example embodiments thereof with reference to the attached drawings, in which.

DETAILED DESCRIPTION

Figure 1:
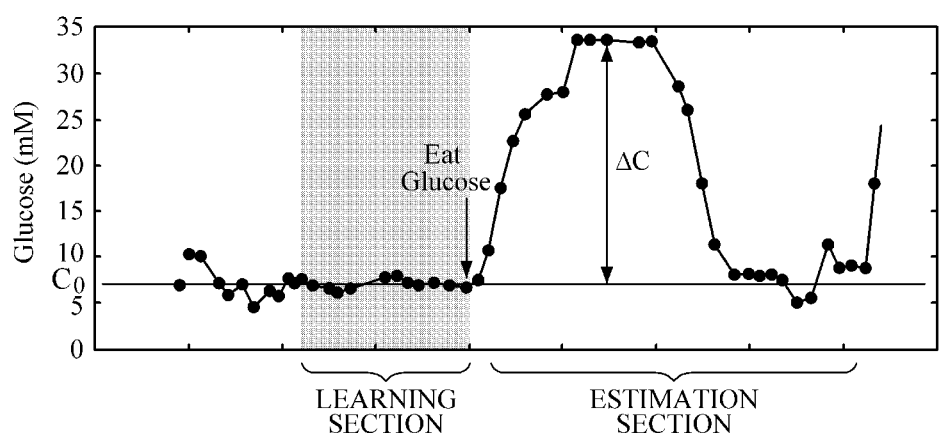
FIG. 1 and FIG. 2 are diagrams for describing a concept of a net analyte signal (NAS) algorithm.

Hereinafter, example embodiments of the disclosure will be described in detail with reference to the accompanying drawings. Throughout the drawings and the detailed description, unless otherwise described, the same drawing reference numerals will be understood to refer to the same elements, features, and structures. The relative size and depiction of these elements may be exaggerated for clarity, illustration, and convenience. In the following description, a detailed description of known functions and configurations incorporated herein will be omitted when it may obscure the subject matter of the disclosure.

Process steps described herein may be performed differently from a specified order, unless a specified order is clearly stated as being necessary in the context of the disclosure. For example, each step may be performed in a specified order, at substantially the same time, in a reverse order, or in any order different from the specified order.

Further, the terms used throughout this specification are defined in consideration of the functions according to example embodiments, and may be varied according to a purpose and an application of the functions and the like. Therefore, definitions of the terms should be understood based on the overall context of the disclosure.

It will be understood that, although the terms first, second, etc. may be used herein to describe various elements, these elements should not be limited by these terms. These terms are only used to distinguish one element from another. Any references to a singular element may include plural elements unless expressly stated otherwise. In the present specification, it should be understood that the terms, such as "including" or "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Further, components that will be described in the specification are discriminated merely according to functions mainly performed by the components. That is, two or more components which will be described later may be integrated into a single component. Furthermore, a single component which will be explained later may be separated into two or more components. Moreover, each component which will be described may additionally perform some or all of a function executed by another component in addition to the main function thereof. Some or all of the main function of each component which will be explained may be carried out by another component. Each component may be implemented as hardware, software, or a combination of both.

Figure 2:
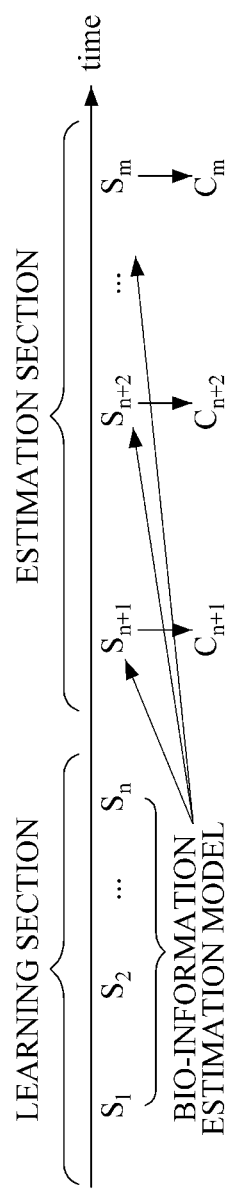

FIGS. 1 and 2 are diagrams for describing a concept of a net analyte signal (NAS) algorithm.

Referring to FIGS. 1 and 2, an NAS algorithm may establish a bio-information estimation model by learning change factors of a spectrum, that are irrelevant to the change in bio-information, of in vivo spectra $S_1, S_2, \ldots,$ and $S_n$ measured during a learning section as learning data. In addition, the NAS algorithm may estimate bio-information $C_{n+1}, C_{n+2},$ and $C_m$ using in vivo spectra $S_{n+1}, S_{n+2}, \ldots,$ and $S_m$ measured during an estimation section after the learning interval and the bio-information estimation model. In this case, the learning section may be a section (e.g., a fasting section) during which the bio-information is not substantially changed.

That is, the NAS algorithm may be employed to establish the bio-information estimation model based on the in vivo spectra measured during the learning section and then estimate the bio-information by applying the bio-information estimation model to the estimation section. Therefore, when at least one of change factors of the spectra irrelevant to the bio-information is changed by, for example, a temperature change of an object, a pressure change between the object and a device, or the like at a certain time point in the estimation section, a residual spectrum may increase from that certain time point so that bio-information estimation error may occur or increase. A residual spectrum may indicate a difference between an actually measured in vivo spectrum and an in vivo spectrum reconstructed using the bio-information estimation model.

Figure 3:
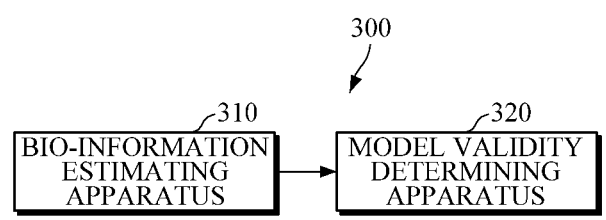
FIG. 3 is a diagram illustrating a bio-information measuring apparatus for measuring bio-information according to an example embodiment.

FIG. 3 is a diagram illustrating a bio-information measuring apparatus for measuring bio-information according to an example embodiment.

The bio-information measuring apparatus shown in FIG. 3 may be an apparatus capable of measuring bio-information of an object by analyzing in vivo spectra of the object and may be configured as a separate apparatus which is mounted in an electronic device or surrounded by a housing. The electronic device may include a mobile phone, a smartphone, a tablet computer, a notebook computer, a personal digital assistant (PDA), a portable multimedia player (PMP), a navigation device, an MP3 player, a digital camera, a wearable device, and the like. The wearable device may include a wristwatch type, a wristband type, a ring-type, a belt type, a necklace type, an ankle band type, a thigh band type, a forearm band type, and the like. However, the electronic device and the wearable device are not limited to the aforementioned examples.

The bio-information may be information about a concentration of an in vivo analyte and the in vivo analyte may include glucose, triglyceride, urea, uric acid, lactate, proteins, cholesterol, antioxidants (e.g., vitamins, carotenoids, flavonoids, ascorbic acid, tocopherol, and the like), ethanol, and the like, but is not limited thereto. When the in vivo analyte is glucose, the bio-information may be a blood glucose level. Hereinafter, for convenience of description, an example embodiment in which the bio-information is a blood glucose level will be described.

Referring to FIG. 3, a bio-information measuring apparatus 300 may include a bio-information estimating apparatus 310 for estimating bio-information and a model validity determining apparatus 320 for determining validity of the bio-information estimation model. Here, the bio-information estimating apparatus 310 and the model validity determining apparatus 320 may be individually implemented as separate hardware devices or be implemented as a single hardware device.

The bio-information estimating apparatus 310 may acquire an in vivo spectrum of an object. In this case, the in vivo spectrum may be an absorption spectrum, a reflection spectrum, or a transmission spectrum. For example, the bio-information estimating apparatus 310 may acquire an in vivo spectra (hereinafter, referred to as an in vivo spectrum for use in learning) measured during a section (e.g., a fasting section) during which a blood glucose level is not substantially changed in the object and/or an in vivo spectrum (hereinafter referred to as an in vivo spectrum for use in estimation) measured for estimating the blood glucose level of the object.

According to an example embodiment, the bio-information estimating apparatus 310 may acquire the in vivo spectrum by receiving the same from an external device that measures and/or stores therein an in vivo spectrum. In this case, the bio-information estimating apparatus 310 may use a wired/wireless communication technology. Here, the wireless communication technology may include Bluetooth communication, Bluetooth low energy (BLE) communication, near field communication (NFC), wireless local access network (WLAN) communication, ZigBee communication, infrared data association (IrDA) communication, wireless fidelity (Wi-Fi) direct (WFD) communication, ultra-wideband (UWB) communication, Ant+ communication, Wi-Fi communication, radio frequency identification (RFID) communication, third generation (3G) communication, fourth generation (4G) communication, and fifth generation (5G) communication, but is not limited thereto.

According to another example embodiment, the bio-information estimating apparatus 310 may emit light towards the object and receive light reflected by or scattered from the object to directly measure an in vivo spectrum, thereby acquiring the in vivo spectrum. In this case, the bio-information estimating apparatus 310 may use an infrared spectroscopy or a Raman spectroscopy, but is not limited thereto and the bio-information estimating apparatus 310 may measure an in vivo spectrum using various spectroscopy methods.

The bio-information estimating apparatus 310 may include a light source configured to emit light towards the object and a photodetector configured to measure an in vivo spectrum by receiving light reflected by or scattered from the object. The light source may emit near infrared (NIR) or mid infrared (MIR) rays towards the object. However, a wavelength of light to be emitted from the light source may be changed depending on the purpose of measurement or the type of bio-information. In addition, the light source may be configured as a single light emitter or may be configured as a set of a plurality of light emitters. The light source may be configured as a light emitting diode (LED), a laser diode, a phosphor, or the like. The photodetector may be configured as a photodiode, a photo transistor, an image sensor (e.g., charge-coupled device (CCD), complementary metal oxide semiconductor (CMOS), or the like), or the like. The photodetector may be configured as a single device or configured in the form of an array of a plurality of photodetectors. The number and arrangement of the light source and the photodetector may vary and may be changed depending on the type of bio-information, the purpose of application, the size and shape of the electronic device in which the bio-information estimating apparatus 310 is mounted, and the like.

The bio-information estimating apparatus 310 may generate a bio-information estimation model. According to an example embodiment, when a plurality of in vivo spectra for leaning are acquired, the bio-information estimating apparatus 310 may generate the bio-information estimation model based on the plurality of acquired in vivo spectra for use in learning. For example, the bio-information estimating apparatus 310 may generate a bio-information estimation model through a NAS algorithm using the plurality of acquired in vivo spectra for use in learning. Specifically, the bio-information estimating apparatus 310 may identify a change factor of a spectrum that is irrelevant to the change in the bio-information by using a plurality of in vivo spectra for use in learning which are measured during a fasting section as learning data. For example, the bio-information estimating apparatus 310 may use various dimension reduction algorithms, such as principle component analysis (PCA), independent component analysis (ICA), non-negative matrix factorization (NMF), and singular value decomposition (SVD), to extract a main component spectrum from the plurality of in vivo spectra for leaning which are measured during a fasting section. In addition, the bio-information estimating apparatus 310 may generate the bio-information estimation model based on a learning result, that is, the extracted main component spectrum. In this case, the generated bio-information estimation model may be represented by Equation 1 and Equation 2 shown below.

$$\begin{bmatrix} C_1 \\ C_2 \\ \vdots \\ C_k \\ \Delta C_g \end{bmatrix} = \begin{bmatrix} PC_1 \\ PC_2 \\ \vdots \\ PC_k \\ \varepsilon_g \end{bmatrix}^{-1} \times S_{skin}/L \quad (1)$$

$$C_g = \Delta C_g + C_{g0} \quad (2)$$

Here, $C_1$, $C_2$, and $C_k$ may denote concentrations of main components, $\Delta C_g$ may denote the amount of an increase in a blood glucose level compared to a baseline blood glucose level, $PC_1$, $PC_2$, and $PC_k$ may denote vectors representing main component spectra, $\varepsilon_g$ may denote a vector representing a spectrum of glucose (hereinafter referred to as a pure component spectrum) of unit concentration (e.g., 1 mM), $S_{skin}$ may denote a vector representing an in vivo spectrum for use in estimation, L may denote a length of a light path, and k may denote the number of main components. In addition, $C_g$ may denote an estimated blood glucose level and $C_g^0$ may denote the baseline blood glucose level (e.g., a blood glucose level measured during a fasting interval). $\varepsilon_g$ may be experimentlaly obtained.

When the bio-information estimating apparatus 310 acquires an in vivo spectrum for use in estimation for blood glucose estimation after generating the bio-information estimation model, the bio-information estimating apparatus 310 may estimate a blood glucose level of the object and concentrations of the main components using the in vivo spectrum for use in estimation and the bio-information estimation model. For example, the bio-information estimating apparatus 310 may estimate the blood glucose level $C_g$ and the concentrations $C_1$, $C_2$, and $C_k$ of the main components using Equations 1 and 2 described above.

The model validity determining apparatus 320 may determine validity of the bio-information estimating model. For example, the model validity determining apparatus 320 may acquire the in vivo spectrum for use in estimation and the blood glucose level and concentrations of the main components that are estimated by using the in vivo spectrum and the bio-information estimation model, and may acquire a residual spectrum of the in vivo spectrum for use in estimation based on the in vivo spectrum for use in estimation, blood glucose level, and concentrations of the main components acquired. In addition, the model validity determining apparatus 320 may determine validity of the bio-information estimation model by using the acquired residual spectrum.

Figure 4:
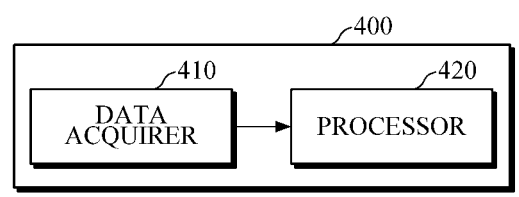
FIG. 4 is a diagram illustrating a model validity determining apparatus according to an example embodiment.

FIG. 4 is a diagram illustrating a model validity determining apparatus according to an example embodiment. The model validity determining apparatus 400 of FIG. 4 may be an example embodiment of the model validity determining apparatus 320 of FIG. 3.

Referring to FIG. 4, the model validity determining apparatus 400 may include a data acquirer 410 and a processor 420.

The data acquirer (or data acquirer interface) 410 may acquire, from a bio-information estimating apparatus, an in vivo spectrum for use in estimation and a blood glucose level and concentrations of main components that are estimated using the in vivo spectrum for use in estimation and a bio-information estimation model. For example, the data acquirer 410 may be a wired or wireless communication interface configured using any combination of hardware and software to acquire the in vivo spectrum for use in estimation, the blood glucose level, and the concentrations of main components from the bio-information estimating apparatus using a wired/wireless communication technology. Here, the data acquirer 410 may be a wireless transceiver configured to communicate according to one or more protocols of the wireless communication technology, which may include Bluetooth communication, BLE communication, NFC, WLAN communication, ZigBee communication, IrDA communication, WFD communication, UWB communication, Ant+ communication, Wi-Fi communication, RFID communication, 3G communication, 4G communication, and 5G communication, but is not limited thereto. The data acquirer 410 may be implemented as a wired communication interface, such as an Ethernet interface, a USB interface, etc. configured to communicate according to one or more communication protocols associated with the wired communication interface, such as Ethernet, TCP/IP, USB 2.0, etc.

The processor 420 may control an overall operation of the model validity determining apparatus 400.

The processor 420 may control the data acquirer 410 to acquire a blood glucose level and concentrations of main components which are estimated using an in vivo spectrum, the in vivo spectrum for use in estimation, and the bio-information estimation model, according to a predetermined period or a user's request.

The processor 420 may acquire a residual spectrum of the in vivo spectrum for use in estimation. For example, the processor 420 may reconstruct an in vivo spectrum for use in estimation using Equation 3 shown below based on the in vivo spectrum for use in estimation, the blood glucose level, and the concentrations of main components, and acquire the residual spectrum of the in vivo spectrum for use in estimation using Equation 4 shown below.

$$S_{recon} = \begin{bmatrix} PC_1 \\ PC_2 \\ \vdots \\ PC_k \\ \varepsilon_g \end{bmatrix} \times \begin{bmatrix} C_1 \\ C_2 \\ \vdots \\ C_k \\ \Delta C_g \end{bmatrix} \times L \quad (3)$$

$$S_{residual} = S_{skin} - S_{recon} \quad (4)$$

Here, $S_{recon}$ may denote a vector representing a reconstructed in vivo spectrum for use in estimation, $PC_1$, $PC_2$, and $PC_k$ may denote vectors reprensenting spectra of main components used in generating a bio-information estimation model, $\varepsilon_g$ may denote a vector representing a spectrum of a pure component used in generating a bio-information estimation model, $C_1$, $C_2$, and $C_k$ are concentrations of main components, $\Delta C_g$ may denote the amount of an increase in a blood glucose level compared to a baseline blood glucose level (e.g., a blood glucose level measured during a fasting interval), L may denote a length of a light path, $S_{skin}$ may denote a vector representing an in vivo spectrum for use in estimation, and $S_{residual}$ may denote a vector representing a residual spectrum.

The description has been made with respect to an example embodiment in which the processor 420 acquires, from the bio-information estimating apparatus, the in vivo spectrum for use in estimation and the blood glucose level and concentrations of the main components which are estimated based on the in vivo spectrum for use in estimation and the bio-information estimation model and acquires the residual spectrum of the in vivo spectrum for use in estimation based on the estimated blood glucose level and concentrations of the main components, but the disclosure is not limited thereto. That is, the processor 420 may acquire the in vivo spectrum for use in estimation, estimate the blood glucose level and the concentrations of the main components based on the acquired in vivo spectrum for use in estimation and the bio-information estimation model, and then acquire the residual spectrum of the in vivo spectrum for use in estimation based on the estimated blood glucose level and concentrations of the main components.

The processor 420 may determine validity of the bio-information estimation model by monitoring the change in shape of the residual spectrum over time.

According to an example embodiment, the processor 420 may select one or more previous residual spectra as reference residual spectra and determine the change in shape of the residual spectrum over time based on similarities between each of the selected reference residual spectra and the currently acquired residual spectrum. In this case, the previous residual spectrum may be a residual spectrum of an in vivo spectrum for use in estimation that is measured before measuring the currently acquired in vivo spectrum for use in estimation.

Also, the processor 420 may determine that the bio-information estimation model is invalid when a result of determining the change in shape of the residual spectrum over time indicates that the amount of change in shape exceeds a predetermined first reference value compared to the amount of change in shape of the reference residual spectrum. For example, the processor 420 may determine that the bio-information estimation model is invalid when the similarity between the reference residual spectrum and the residual spectrum of the in vivo spectrum for use in estimation is smaller than a second reference value, wherein the second reference value of the similarity corresponds to the predetermined first reference value of the change in shape of the residual spectrum. In this case, the processor 420 may use various similarity calculation algorithms, such as Euclidean distance, Manhattan Distance, cosine distance, Mahalanobis Distance, Jaccard coefficient, extended Jaccard coefficient, Pearson's correlation coefficient, Spearman's correlation coefficient, and the like.

According to an example embodiment, the processor 420 may generate a similarity map based on the similarities between each of the previous residual spectra and the current residual spectrum and monitor the change in shape of the residual spectrum over time using the generated similarity map.

According to an example embodiment, the processor 420 may further use a size of the vector representing the residual spectrum when determining the validity of the bio-information estimation model. For example, the processor 420 may determine whether the size of the vector representing the residual spectrum is greater than a predetermined reference value, and may determine final validity based on a combination of a result of determination that the size of the vector representing the residual spectrum and a result of determination based on the change in shape of the residual spectrum over time. That is, the processor 420 may determine that the bio-information estimation model is invalid when the size of the vector representing the residual spectrum is greater than the predetermined reference value and the similarity between the reference residual spectrum and the residual spectrum of the in vivo spectrum for use in estimation is smaller than the second reference value. Alternatively, the processor 420 may determine that the bio-information estimation model is invalid when the size of the vector representing the residual spectrum is greater than the predetermined reference value.

When it is determined that the bio-information estimation model is invalid, the processor 420 may provide the determination result to the user or the bio-information estimating apparatus such that the bio-information estimating apparatus may update or regenerate the bio-information estimation model.

Figure 5A:
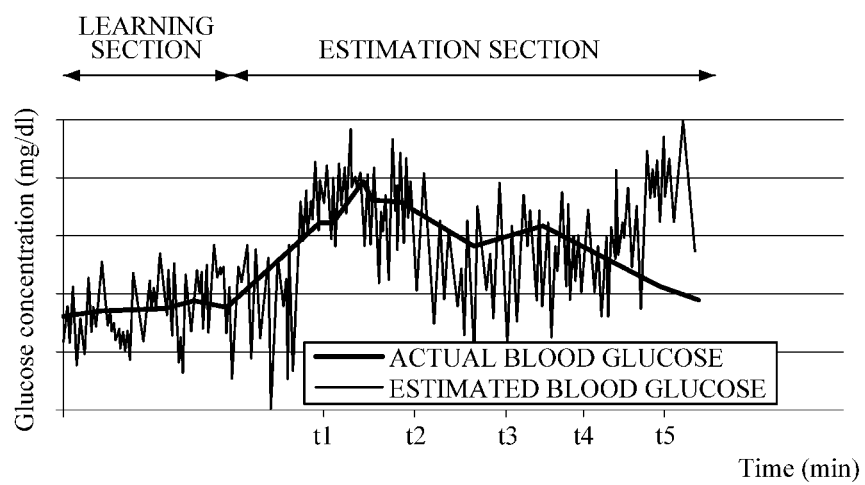
FIGS. 5A and 5B are graphs for describing a relationship between the change in shape of a residual spectrum and the validity of a bio-information estimation model.
Figure 5B:
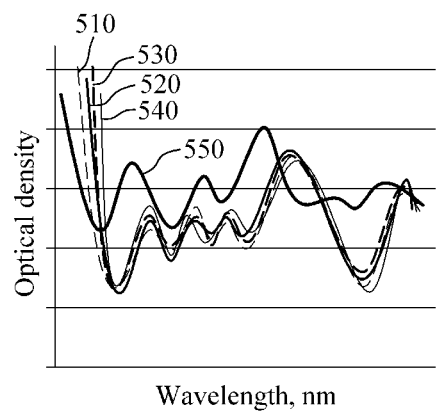

FIGS. 5A and 5B are graphs for describing a relationship between the change in shape of a residual spectrum and the validity of the bio-information estimation model. More specifically, FIG. 5A shows graphs of an estimated blood glucose level and an actual blood glucose level and FIG. 5B shows graphs of residual spectra of in vivo spectra measured at each point in time.

Referring to FIG. 5A, at least one of change factors of a spectrum irrelevant to a blood glucose level may change at any point in time after a tie point t4 in an estimation section and thereby a blood glucose estimation error may be increased from that point of time. In this case, the bio-information estimation model becomes no longer valid on or after the time point t4.

FIG. 5B shows a residual spectrum 510 of an in vivo spectrum for use in estimation which is measured at t1, a residual spectrum 520 of the in vivo spectrum for use in estimation which is measured at t2, a residual spectrum 530 of the in vivo spectrum for use in estimation which is measured at t3, and a residual spectrum 540 of the in vivo spectrum for use in estimation which is measured at t4. As shown in FIG. 5B, the residual spectra 510, 520, 530, and 540 are similar in shape to one another and hence the shape changes therebetween are not significant. However, a residual spectrum 550 of the in vivo spectrum for use in estimation which is measured at t5 is not similar to other residual spectra 510, 520, 530, and 540, and hence the shape change between the residual spectrum 550 and the residual spectra 510, 520, 530, and 540 is significant as compared to the shape changes between residual spectra 510, 520, 530, and 540.

Therefore, it can be seen that the change in shape of the residual spectrum over time and the validity of the bio-information estimation model are significantly related to each other, and the model validity determining apparatus may determine the validity of the bio-information estimation model by monitoring the change in shape of the residual spectrum over time. The model validity determining apparatus may select one or more previous residual spectra 510, 520, 530, and 540 as reference residual spectra and determine the bio-information estimation model as invalid based on the similarity between the change in shape of the residual spectrum 550 and the change in shape of the reference residual spectra is a smaller than a preset reference value.

Figure 6:
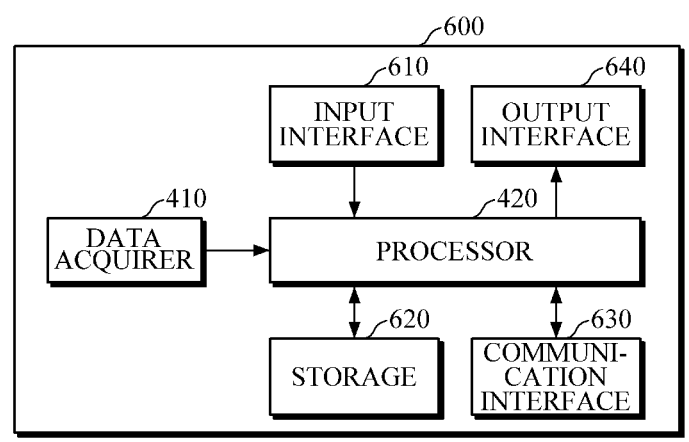
FIG. 6 is a diagram illustrating a model validity determining apparatus according to another example embodiment.

FIG. 6 is a diagram illustrating a model validity determining apparatus according to another example embodiment. The model validity determining apparatus 600 of FIG. 6 may be another example embodiment of the model validity determining apparatus 320 of FIG. 3.

Referring to FIG. 6, the model validity determining apparatus 600 may include a data acquirer 410, a processor 420, an input interface 610, a storage 620, a communication interface 630, and an output interface 640. Here, the data acquirer 410 and the processor 420 are substantially the same or similar to those described with reference to FIG. 4, and hence detailed descriptions thereof will not be reiterated.

The input interface 610 may receive various operation signals based on a user input. According to an example embodiment, the input interface 610 may include a key pad, a dome switch, a touch pad (e.g., a static pressure touch pad, a capacitive touch page, or the like), a jog wheel, a jog switch, a hardware button, and the like. In particular, when a touch pad has a layered structure with a display, this structure may be referred to as a touch screen.

Programs or commands for operation of the model validity determining apparatus 600 may be stored in the storage 620, and data input to the model validity determining apparatus 600 and processing result data of the model validity determining apparatus 600 may be stored therein. The storage 620 may include at least one type of storage medium, such as a flash memory type, a hard disk type, a multimedia card micro type, a card type memory (e.g., a secure digital (SD) memory or an eXtreme digital (XD) memory) random access memory (RAM), static random access memory (SRAM), read-only memory (ROM), electrically erasable programmable read-only memory (EEPROM), programmable read-only memory(PROM), a magnetic memory, a magnetic disk, an optical disk, and the like. In addition, the model validity determining apparatus 600 may operate in association with an external storage medium, such as a web storage that performs the storage function of the storage 620 via the Internet.

The communication interface 630 may communicate with an external device. For example, the communication interface 630 may transmit the input data, the stored data, the processed data, and the like of the model validity determining apparatus 600 to the external device, or may receive a variety of data to determine the validity of the bio-information estimation model from the external device.

In this case, the external device may be medical equipment using the input data, the stored data, the processed data, and the like of the model validity determining apparatus 600, a printer to print out results, or a display device to display the results. In addition, the external device may be a digital television (TV), a desktop computer, a mobile phone, a smartphone, a tablet computer, a notebook computer, a personal digital assistant (PDA), a portable multimedia player (PMP), a navigation device, an MP3 player, a digital camera, a wearable device, or the like, but is not limited thereto.

The communication interface 630 may communicate with the external device using a wired/wireless communication technology. Here, the wireless communication technology may include Bluetooth communication, BLE communication, NFC, WLAN communication, ZigBee communication, IrDA communication, WFD communication, UWB communication, Ant+ communication, Wi-Fi communication, RFID communication, 3G communication, 4G communication, and 5G communication, but is not limited thereto.

The output interface 640 may output the input data, the stored data, the processed data, and the like of the model validity determining apparatus 600. According to an example embodiment, the output interface 640 may output the input data, the stored data, the processed data, and the like of the model validity determining apparatus 600 by using at least one of an acoustic method, a visual method, and a tactile method. To this end, the output interface 640 may include a speaker, a display, a vibrator, and the like.

Figure 7:
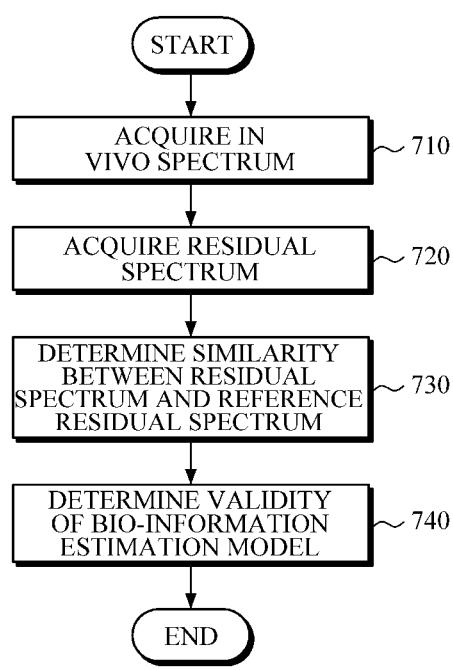
FIG. 7 is a flowchart illustrating a method of determining validity of a bio-information estimation model according to an example embodiment.

FIG. 7 is a flowchart illustrating a method of determining validity of a bio-information estimation model according to an example embodiment. The method of FIG. 7 for determining validity of a bio-information estimation model may be performed by the bio-information measuring apparatus 300 of FIG. 3.

Referring to FIG. 7, the bio-information measuring apparatus may acquire an in vivo spectrum of an object for use in estimation (710). For example, the bio-information estimating apparatus may acquire the in vivo spectrum for use in estimation by receiving the same from an external device that measures and/or stores the in vivo spectrum or may directly measure the in vivo spectrum for use in estimation by emitting light towards the object and receiving light reflected by or scattered from the object.

The bio-information measuring apparatus may acquire a residual spectrum of the in vivo spectrum for use in estimation by using a bio-information estimation model (720). According to an example embodiment, the bio-information estimating apparatus may estimate a blood glucose level of the object and concentrations of main components by using the in vivo spectrum for use in estimation and a bio-information estimation model, and reconstruct an in vivo spectrum for use in estimation based on the in vivo spectrum for use in estimation and the estimated blood glucose level and concentrations of main components. Also, the bio-information measuring apparatus may acquire a residual spectrum of the in vivo spectrum for use in estimation by using the reconstructed in vivo spectrum for use in estimation. In this case, the bio-information measuring apparatus may use Equations 1 to 4 described above to perform the above-described operations and acquire the residual spectrum of the in vivo spectrum for use in estimation.

The bio-information measuring apparatus may determine a similarity between the acquired residual spectrum and a reference residual spectrum (730). For example, the bio-information measuring apparatus may select one or more previous residual spectra as reference residual spectra and determine a similarity between each of the selected reference residual spectra and the acquired residual spectrum. In this case, the previous residual spectrum may be a residual spectrum of an in vivo spectrum for use in estimation that is measured before measuring the currently acquired in vivo spectrum for use in estimation. The bio-information measuring apparatus may use various similarity calculation algorithms, such as Euclidean distance, Manhattan Distance, cosine distance, Mahalanobis Distance, Jaccard coefficient, extended Jaccard coefficient, Pearson's correlation coefficient, Spearman's correlation coefficient, and the like.

The bio-information measuring apparatus may determine validity of the bio-information estimation model according to a result of determining the similarity between the acquired residual spectrum and the reference residual spectrum (740). For example, the bio-information measuring apparatus may determine that the bio-information estimation model is invalid when the similarity between the acquired residual spectrum and the reference residual spectrum is smaller than a predetermined reference value (e.g., the predetermined second reference value corresponding to the predetermined first reference value of the change in shape of the residual spectrum compared to the amount of change in shape of the reference residual spectrum), and may determine that the bio-information estimation model is valid when the similarity between the acquired residual spectrum and the reference residual spectrum is greater than or equal to the predetermined reference value (e.g., the second reference value).

On the other hand, the bio-information measuring apparatus may further use a size of the vector representing the residual spectrum when determining the validity of the bio-information estimation model. For example, the bio-information measuring apparatus may determine whether the size of the vector representing the residual spectrum is greater than a predetermined reference value, and may determine final validity based on a combination of a result of determination that the size of the vector representing the residual spectrum and the determination result of operation 740. Alternatively, the bio-information measuring apparatus may determine that the bio-information estimation model is invalid when the size of the vector representing the residual spectrum is greater than the predetermined reference value.

Figure 8:
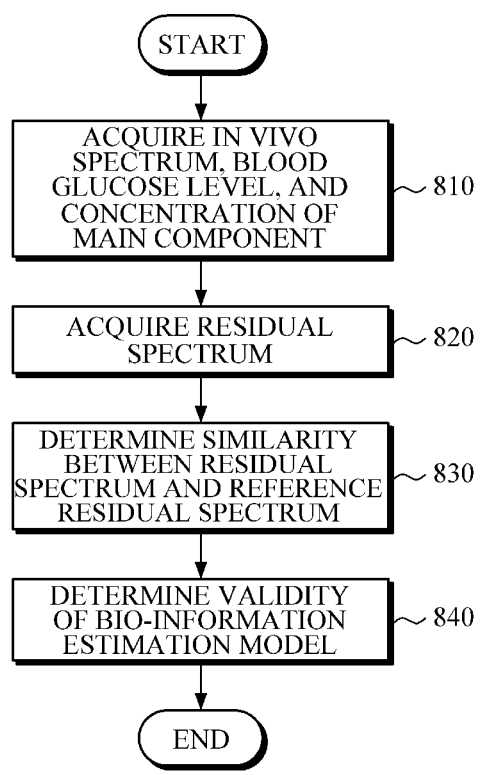
FIG. 8 is a flowchart illustrating a method of determining validity of a bio-information estimation model according to another example embodiment.

FIG. 8 is a flowchart illustrating a method of determining validity of a bio-information estimation model according to another example embodiment. The method of FIG. 8 for determining validity of a bio-information estimation model may be performed by the model validity determining apparatus 400 or 600 of FIG. 4 or 6.

Referring to FIG. 8, the model validity determining apparatus may acquire an in vivo spectrum for use in estimation and a blood glucose level and concentrations of main components which are acquired using the in vivo spectrum for use in estimation (810). For example, the model validity determining apparatus may acquire, from a bio-information estimating apparatus, the in vivo spectrum for use in estimation and the blood glucose level and concentrations of main components which are estimated using the in vivo spectrum for use in estimation and a bio-information estimation model.

The model validity determining apparatus may acquire a residual spectrum of the in vivo spectrum for use in estimation using the in vivo spectrum for use in estimation, the blood glucose level, and the concentrations of main components (820). For example, the model validity determining apparatus may reconstruct an in vivo spectrum for use in estimation using Equation 3, and acquire the residual spectrum of the in vivo spectrum for use in estimation using Equation 4.

The model validity determining apparatus may determine a similarity between the acquired residual spectrum and a reference residual spectrum (830). For example, the model validity determining apparatus may select one or more previous residual spectra as reference residual spectra and determine a similarity between each of the selected reference residual spectra and the acquired residual spectrum. In this case, the model validity determining apparatus may use various similarity calculation algorithms described above.

The model validity determining apparatus may determine validity of the bio-information estimation model based on a result of determining the similarity between the acquired residual spectrum and the reference residual spectrum (840). For example, the model validity determining apparatus may determine that the bio-information estimation model is invalid when the similarity between the acquired residual spectrum and the reference residual spectrum is smaller than a predetermined reference value (e.g., the second reference value), and may determine that the bio-information estimation model is valid when the similarity between the acquired residual spectrum and the reference residual spectrum is greater than or equal to the predetermined reference value (e.g., the second reference value).

On the other hand, the model validity determining apparatus may further use a size of the vector representing the residual spectrum when determining the validity of the bio-information estimation model. For example, the model validity determining apparatus may determine whether the size of the vector representing the residual spectrum is greater than a predetermined reference value, and may determine final validity based on a combination of a result of determination based on the size of the vector representing the residual spectrum and the determination result of operation 840. Alternatively, the model validity determining apparatus may determine that the bio-information estimation model is invalid when the size of the vector representing the residual spectrum is greater than the predetermined reference value.

Figure 9:
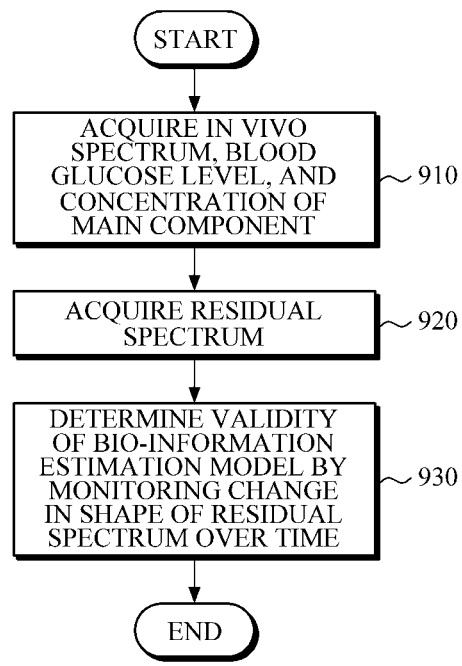
FIG. 9 is a flowchart illustrating a method of determining validity of a bio-information estimation model according to still another example embodiment.

FIG. 9 is a flowchart illustrating a method of determining validity of a bio-information estimation model according to still another example embodiment. The method of FIG. 9 for determining validity of a bio-information estimation model may be performed by the model validity determining apparatus 400 or 600 of FIG. 4 or 6. In FIG. 9, operation 910 and operation 920 are substantially the same or similar to operation 810 and operation 820 of FIG. 8, and hence they will be briefly described.

Referring to FIG. 9, the model validity determining apparatus may acquire an in vivo spectrum for use in estimation and a blood glucose level and concentrations of main components which are estimated using the in vivo spectrum for use in estimation and a bio-information estimation model (910), and may acquire a residual spectrum of the in vivo spectrum for use in estimation using the acquired in vivo spectrum for use in estimation, blood glucose level and concentrations of main components (920).

The model validity determining apparatus may determine validity of the bio-information estimation model by monitoring the change in shape of the residual spectrum over time (930). According to an example embodiment, the model validity determining apparatus may select one or more previous residual spectra as reference residual spectra and determine a similarity between each of the selected reference residual spectra and the acquired residual spectrum. Also, the model validity determining apparatus may determine the change in shape of the residual spectrum over time based on the determined similarities. The model validity determining apparatus may determine that the bio-information estimation model is invalid when the amount of change in shape exceeds a predetermined first reference value compared to the amount of change in shape of the reference residual spectrum, and may determine that the bio-information estimation model is valid when the amount of change in shape is lower than or equal to the predetermined first reference value.

Figure 10:
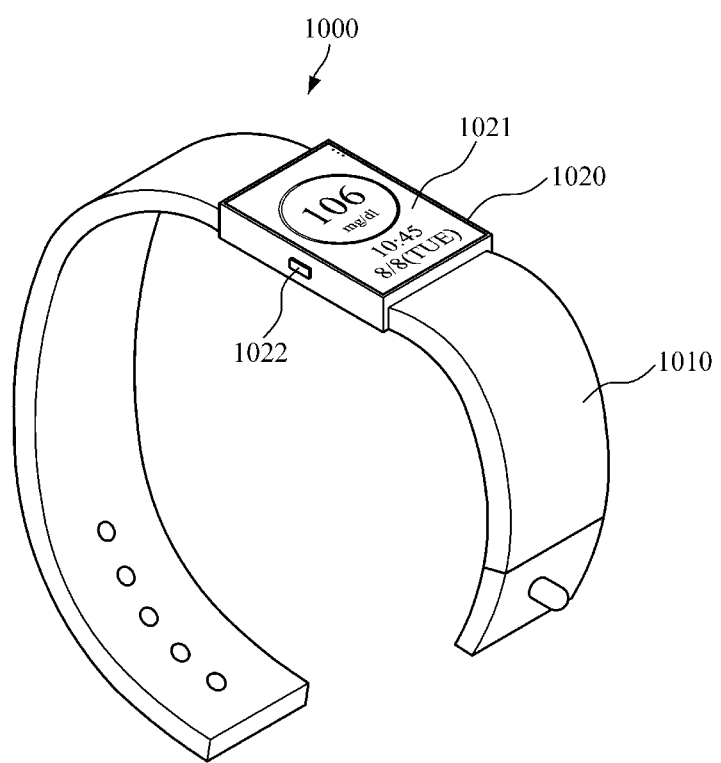
FIG. 10 is a diagram illustrating a wrist wearable device according to an example embodiment.

FIG. 10 is a diagram illustrating a wrist wearable device according to an example embodiment.

Referring to FIG. 10, the wrist wearable device 1000 may include a strap 1010 and a main body 1020.

The strap 1010 may be formed as two sections which are connected at both sides of the main body 1020 to be fastened to each other, or may be integrally formed as a band (e.g., a smart band). The strap 1010 may be made of a flexible material to bend around a user's wrist so that the main body 1020 may be worn around the user's wrist.

The above-described bio-information measuring apparatus 300, the bio-information estimating apparatus 310, and/or the model validity determining apparatus 320, 400, or 600 may be mounted on the main body 1020. In addition, a battery may be equipped in the main body to supply power to the wrist wearable device 1000, the bio-information measuring apparatus 300, the bio-information estimating apparatus 310, and the model validity determining apparatus 320, 400, or 600.

An optical sensor may be mounted at the bottom of the main body 1020 to be exposed to the wrist of the user. In this manner, when the user wears the wrist wearable device 1000, the optical sensor may naturally come into contact with the user's skin. In this case, the optical sensor may be configured to emit light towards an object and acquire an in vivo spectrum by receiving light reflected by or scattered from the object.

The wrist wearable device 1000 may further include a display 1021 and an input interface 1022 that are mounted in the main body 1020. The display 1021 may display the processed data and processing result data of the wrist wearable device 1000, the bio-information measuring apparatus 300, the bio-information estimating apparatus 310, and the model validity determining apparatus 320, 400, or 600. The input interface 1022 may receive various operation signals from the user.

In the related art, when bio-information such as a blood glucose level is obtained by using a non-invasive measurement method using a spectroscope, there is a problem that the obtained bio-information may not be accurate. According to the example embodiments of the disclosure, when a bio-information estimation model is used to estimate bio-information of an object such as a concentration of glucose so that the bio-information can be obtained in a non-invasive manner, the validity of the bio-information estimation model may be accurately determined, thereby increasing accuracy in estimating the bio-information.

The example embodiments may be implemented as a non-transitory computer-readable code stored in a computer-readable recording medium. The computer-readable recording medium may be any type of recording medium in which data is stored in a computer-readable manner.

The disclosure may be implemented as a computer-readable code written on a computer-readable recording medium. Codes and code segments for implementing the disclosure may be easily deduced by one of ordinary skill in the art. The computer-readable recording medium may be any type of recording device in which data is stored in a computer-readable manner. Examples of the computer-readable recording medium include a ROM, a RAM, a CD-ROM, a magnetic tape, a floppy disc, an optical disk, and the like. Further, the computer-readable recording medium may be distributed over a plurality of computer systems connected to a network so that a computer-readable recording medium is written thereto and executed therefrom in a decentralized manner.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the above block diagrams, communication between the components, elements or units may be performed through the bus. Functional aspects of the above example embodiments may be implemented in algorithms that execute on one or more processors. Furthermore, the components, elements or units represented by a block or processing operations may employ any number of related art techniques for electronics configuration, signal processing and/or control, data processing and the like.

The disclosure has been described herein with regard to example embodiments. However, it will be obvious to those skilled in the art that various modifications may be made without departing from the gist of the disclosure. Therefore, it is to be understood that that the scope of the disclosure is not limited to the above-mentioned embodiments, but is intended to include various modifications and equivalents included within the spirit and scope of the appended claims.

What is claimed is:

1. An apparatus for determining a validity of a bio-information estimation model, comprising:
   a data acquirer interface configured to acquire an in vivo spectrum of an object, and acquire bio-information and a concentration of a main component which are estimated based on the in vivo spectrum and the bio-information estimation model; and
   a processor configured to acquire a residual spectrum of the acquired in vivo spectrum based on the acquired in vivo spectrum, the acquired bio-information, and the acquired concentration of the main component, determine a similarity between the acquired residual spectrum and a reference residual spectrum, and determine the validity of the bio-information estimation model based on the determined similarity.

2. The apparatus of claim 1, wherein the processor is configured to reconstruct an in vivo spectrum based on the acquired in vivo spectrum, the acquired bio-information, and the acquired concentration of the main component, and acquire the residual spectrum based on the reconstructed in vivo spectrum and the acquired in vivo spectrum.

3. The apparatus of claim 2, wherein the processor is configured to acquire the residual spectrum by subtracting the reconstructed in vivo spectrum from the acquired in vivo spectrum.

4. The apparatus of claim 1, wherein the bio-information comprises information on a concentration of an analyte, the analyte comprising at least one of glucose, triglyceride, urea, uric acid, lactate, proteins, cholesterols, antioxidants, and ethanol.

5. The apparatus of claim 1, wherein the processor is configured to select, as the reference residual spectrum, a residual spectrum of an in vivo spectrum that is measured prior to measuring the acquired in vivo spectrum.

6. The apparatus of claim 1, wherein the processor is configured to determine that the bio-information estimation model is invalid based on a comparison between the determined similarity and a predetermined reference value.

7. The apparatus of claim 1, wherein the processor is configured to determine the validity of the bio-information estimation model further based on a size of a vector representing the acquired residual spectrum.

8. The apparatus of claim 1, wherein the bio-information estimation model is based on a net analyte signal (NAS) algorithm.

9. An apparatus for determining a validity of a bio-information estimation model, comprising:
   a data acquirer interface configured to acquire an in vivo spectrum of an object, and acquire bio-information and a concentration of a main component which are estimated based on the in vivo spectrum and the bio-information estimation model; and
   a processor configured to acquire a residual spectrum of the acquired in vivo spectrum based on the acquired in vivo spectrum, the acquired bio-information, and the acquired concentration of the main component and determine the validity of the bio-information estimation model by based on a change in shape of the residual spectrum over time.

10. The apparatus of claim 9, wherein the processor is configured to reconstruct an in vivo spectrum based on the acquired in vivo spectrum, the acquired bio-information, and the acquired concentration of the main component and acquire the residual spectrum based on the reconstructed in vivo spectrum and the acquired in vivo spectrum.

11. The apparatus of claim 10, wherein the processor is configured to acquire the residual spectrum by subtracting the reconstructed in vivo spectrum from the acquired in vivo spectrum.

12. The apparatus of claim 9, wherein the bio-information comprises information on a concentration of an analyte, the analyte comprising at least one of glucose, triglyceride, urea, uric acid, lactate, proteins, cholesterols, antioxidants, and ethanol.

13. The apparatus of claim 9, wherein the processor is configured to determine that the bio-information estimation model is invalid based on the change in shape of the residual spectrum over time exceeding a predetermined reference value.

14. The apparatus of claim 9, wherein the processor is configured to determine the change in shape of the residual spectrum based on a similarity between the acquired residual spectrum and a reference residual spectrum.

15. The apparatus of claim 14, wherein the processor is configured to select, as the reference residual spectrum, a residual spectrum of an in vivo spectrum that is measured prior to measuring the acquired in vivo spectrum.

16. The apparatus of claim 9, wherein the processor is configured to determine the validity of the bio-information estimation model further based on a size of a vector representing the acquired residual spectrum.

17. The apparatus of claim 9, wherein the bio-information estimation model is based on a NAS algorithm.

18. A method of determining a validity of a bio-information estimation model, comprising:
   acquiring an in vivo spectrum of an object, and acquiring bio-information and a concentration of a main component which are estimated based on the in vivo spectrum and the bio-information estimation model;
   acquiring a residual spectrum of the acquired in vivo spectrum based on the acquired in vivo spectrum, the acquired bio-information, and the acquired concentration of the main component;
   determining a similarity between the acquired in vivo spectrum and a reference residual spectrum; and determining the validity of the bio-information estimation model based on the determined similarity.

19. The method of claim 18, wherein the acquiring the residual spectrum comprises reconstructing an in vivo spectrum based on the acquired in vivo spectrum, the acquired bio-information, and the acquired concentration of the main component, and acquiring the residual spectrum based on the reconstructed in vivo spectrum and the acquired in vivo spectrum.

20. The method of claim 19, wherein the acquiring the residual spectrum comprises acquiring the residual spectrum by subtracting the reconstructed in vivo spectrum from the acquired in vivo spectrum.

21. The method of claim 18, wherein the bio-information comprises information on a concentration of an analyte, the analyte comprising at least one of glucose, triglyceride, urea, uric acid, lactate, proteins, cholesterols, antioxidants, and ethanol.

22. The method of claim 18, wherein the determining the validity comprises selecting, as the reference residual spectrum, a residual spectrum of an in vivo spectrum that is measured prior to measuring the acquired in vivo spectrum.

23. The method of claim 18, wherein the determining the validity comprises determining that the bio-information estimation model is invalid based on the determined similarity being smaller than a predetermined reference value.

24. The method of claim 18, wherein the determining the validity comprises determining the validity of the bio-information estimation model further based on a size of a vector representing the acquired residual spectrum.

25. The method of claim 18, wherein the bio-information estimation model is based on a NAS algorithm.

26. A method of determining a validity of a bio-information estimation model, comprising:
    acquiring an in vivo spectrum of an object, and acquiring bio-information and a concentration of a main component which are estimated based on the in vivo spectrum and the bio-information estimation model;
    acquiring a residual spectrum of the acquired in vivo spectrum based on the acquired in vivo spectrum, the acquired bio-information, and the acquired concentration of the main component; and
    determining the validity of the bio-information estimation model based on a change in shape of the residual spectrum over time.

27. The method of claim 26, wherein the acquiring the residual spectrum comprises reconstructing an in vivo spectrum based on the acquired in vivo spectrum, the acquired bio-information, and the acquired concentration of the main component and acquiring the residual spectrum based on the reconstructed in vivo spectrum and the acquired in vivo spectrum.

28. The method of claim 27, wherein the acquiring the residual spectrum comprises acquiring the residual spectrum by subtracting the reconstructed in vivo spectrum from the acquired in vivo spectrum.

29. The method of claim 26, wherein the bio-information comprises information on a concentration of an analyte, the analyte comprising at least one of glucose, triglyceride, urea, uric acid, lactate, proteins, cholesterols, antioxidants, and ethanol.

30. The method of claim 26, wherein the determining the validity of the bio-information estimation model comprises determining that the bio-information estimation model is invalid based on the change in shape of the residual spectrum over time exceeding a predetermined reference value.

31. The method of claim 26, wherein the determining the validity comprises determining the change in shape of the residual spectrum over time based on a similarity between the acquired residual spectrum and a reference residual spectrum.

32. The method of claim 31, wherein the determining the validity comprises selecting, as the reference residual spectrum, a residual spectrum of an in vivo spectrum that is measured prior to measuring the acquired in vivo spectrum.

33. The method of claim 26, wherein the determining the validity of the bio-information estimation model comprises determining the validity of the bio-information estimation model further based on a size of a vector representing the acquired residual spectrum.

34. The method of claim 26, wherein the bio-information estimation model is based on a NAS algorithm.

35. A method of determining a validity of a bio-information estimation model, comprising:
    acquiring an in vivo spectrum of an object;
    acquiring a residual spectrum of the acquired in vivo spectrum based on the bio-information estimation model;
    determining a similarity between the acquired residual spectrum and a reference residual spectrum; and
    determining the validity of the bio-information estimation model based on the determined similarity.

36. The method of claim 35, wherein the bio-information estimation model is based on a NAS algorithm.

37. The method of claim 35, wherein the acquiring the residual spectrum comprises estimating bio-information of the object and a concentration of a main component based on the acquired in vivo spectrum and the bio-information estimation model, reconstructing an in vivo spectrum based on the acquired in vivo spectrum, the estimated bio-information, and the estimated concentration of the main component, and acquiring the residual spectrum based on the reconstructed in vivo spectrum and the acquired in vivo spectrum.

38. The method of claim 37, wherein the acquiring the residual spectrum comprises acquiring the residual spectrum by subtracting the reconstructed in vivo spectrum from the acquired in vivo spectrum.

* * * * *